US007449307B2

(12) United States Patent

Cima et al.

(10) Patent No.: US 7,449,307 B2
(45) Date of Patent: *Nov. 11, 2008

(54) RAISED SURFACE ASSAY PLATE

(75) Inventors: Michael Cima, Winchester, MA (US); Wendy Pryce Lewis, Watertown, MA (US); Javier Gonzalez-Zugasti, N Billerica, MA (US); J. Richard Gyory, Sudbury, MA (US); Anthony V. Lemmo, Sudbury, MA (US); Julie Monagle, Watertown, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 712 days.

This patent is subject to a terminal disclaimer.

(21) Appl. No.: 10/694,639

(22) Filed: Oct. 27, 2003

(65) Prior Publication Data

US 2004/0142460 A1 Jul. 22, 2004

Related U.S. Application Data

(63) Continuation-in-part of application No. 10/439,943, filed on May 16, 2003, now Pat. No. 6,908,760, which is a continuation-in-part of application No. 10/282,505, filed on Oct. 28, 2002, now Pat. No. 6,852,526.

(60) Provisional application No. 60/428,164, filed on Nov. 21, 2002.

(51) Int. Cl.

| | |
|---|---|
| ***A61K 9/70*** | (2006.01) |
| ***G01N 13/04*** | (2006.01) |
| ***G01N 1/28*** | (2006.01) |
| ***C12Q 1/24*** | (2006.01) |

(52) U.S. Cl. .................. 435/40.52; 435/30; 435/288.4; 435/297.5; 424/9.2; 424/449; 604/304; 604/307; 73/64.47

(58) Field of Classification Search .............. 435/288.4, 435/288.5, 297.5, 30, 40.52; 604/304, 307; 424/9.2; 73/64.47
See application file for complete search history.

(56) References Cited

U.S. PATENT DOCUMENTS 3,107,204 A 10/1963 Brown et al.

(Continued)

FOREIGN PATENT DOCUMENTS

WO WO 02/06518 1/2002

(Continued)

OTHER PUBLICATIONS

Patrick et al. (1997) "Effect of vehicles on topical delivery of 5-fluorouracil (5FU) by 1-acyl-5FU prodrugs" *Intl. J. Pharmaceutics* 154:39-48.

*Primary Examiner*—William H Beisner
(74) *Attorney, Agent, or Firm*—Workman Nydegger

(57) ABSTRACT

The assay plate includes a substrate having an substrate surface and at least one raised pad extending from the substrate surface. The raised pad includes a substantially planar sample receiving surface configured for holding a sample thereon for in situ experimentation. The sample receiving surface preferably has at least one sharp edge at the junction between a sidewall coupling the sample receiving surface to the substrate surface. The sample receiving surface is preferably a circle, oval, square, rectangle, triangle, pentagon, hexagon, or octagon shape that is sized to hold a predetermined volume of the sample. A method of using the above described assay plate is also provided. Once a raised pad extending from a substrate is formed, a sample is deposited on the raised pad. Experiments are subsequently performed using the sample on the raised pad.

11 Claims, 9 Drawing Sheets

U.S. PATENT DOCUMENTS 3,654,047 A * 4/1972 Berkowitz .................. 428/179
3,837,340 A * 9/1974 Counter ...................... 604/307
3,893,891 A 7/1975 Tannenbaum et al.
4,045,291 A 8/1977 Berger
4,235,687 A 11/1980 Romette et al.
4,317,726 A 3/1982 Shepel
4,390,027 A * 6/1983 Alani et al. ................. 600/556
4,468,321 A 8/1984 St. John
4,667,504 A 5/1987 Hobson
4,686,190 A 8/1987 Cramer et al.
4,771,004 A 9/1988 Higuchi et al.
4,835,102 A 5/1989 Bell et al.
4,863,696 A 9/1989 Saydek et al.
4,887,611 A * 12/1989 Rudiger et al. .............. 600/556
4,912,057 A 3/1990 Guirguis et al.
4,912,060 A 3/1990 Fein
5,182,216 A 1/1993 Clayton et al.
5,306,467 A 4/1994 Douglas-Hamilton
5,325,864 A * 7/1994 Gerber ....................... 600/556
5,474,783 A 12/1995 Miranda et al.
5,490,415 A 2/1996 Mak et al.
5,503,843 A 4/1996 Santus et al.
5,789,240 A 8/1998 Abdulrazik et al.
5,814,599 A 9/1998 Mitragotri et al.
5,947,921 A 9/1999 Johnson et al.
5,962,250 A 10/1999 Gavin et al.
6,002,961 A 12/1999 Mitragotri et al.
6,018,678 A 1/2000 Mitragotri et al.
6,022,700 A 2/2000 Monks et al.
6,041,253 A 3/2000 Kost et al.
6,043,027 A 3/2000 Selick et al.
6,087,157 A 7/2000 Badylak et al.
6,171,780 B1 1/2001 Pham et al.
6,190,315 B1 2/2001 Kost et al.
6,234,990 B1 5/2001 Rowe et al.
6,758,099 B2 7/2004 Cima et al.
6,766,817 B2 7/2004 da Silva ......................... 137/1
6,890,488 B2 * 5/2005 Mathus et al. ................ 422/99
6,908,760 B2 * 6/2005 Cima et al. .............. 435/288.4
2001/0046682 A1 11/2001 Lichtenwalter
2001/0056255 A1 12/2001 Kost et al.
2002/0045850 A1 4/2002 Rowe et al.
2003/0124029 A1 7/2003 Webb et al.
2004/0087007 A1 5/2004 Cima et al.

FOREIGN PATENT DOCUMENTS

WO WO 02/16941 2/2002

* cited by examiner

RAISED SURFACE ASSAY PLATE

RELATED APPLICATIONS

This application is a continuation-in-part of U.S. patent application Ser. No. 10/439,943 filed May 16, 2003, now U.S. Pat. No. 6,908,760 which claims the benefit of U.S. Provisional Patent Application No. 60/428,164, filed Nov. 21, 2002. This application is also a continuation-in-part of U.S. patent application Ser. No. 10/282,505, filed Oct. 28, 2002 now U.S. Pat. No. 6,852,526. Each of these applications is hereby incorporated by reference for all purposes.

BACKGROUND OF THE INVENTION

1. Field of the Invention

The invention relates generally to a device used for the testing of physical, chemical, biological or biochemical properties, characteristics, or reactions. More particularly, the invention is directed to an assay plate having an array of raised pads or plateaus for receiving samples thereon.

2. Description of Related Art

Assay plates, otherwise know as assay trays, sample trays, microtiter plates, microplates, well plates, or multi-well test plates, are well known in the art. These assay plates are generally used for chemical or biological experiments, such as the parallel detection and monitoring of biological or chemical reactions, cell growth, virus isolation, titration, toxicity tests, characterization testing, crystallization, or combinatorial synthesis or testing of reactants.

Over the years, many assay plate geometries have been developed to hold samples during such chemical or biological experiments. Most of these assay plate geometries, however, generally include an array or matrix of small sample holding cavities, indentations, or wells.

However, these assay plates with cavities or wells have a number of drawbacks. For example, organic solvent-based fluids tend to wet the sides of the wells due wicking, or more precisely capillary action, changing the geometry of the fluid volume (surface area, pathlength), and can cause fluid to come out of the cavity. Also, the walls defining the wells, although often transparent, interfere with viewing the samples in the wells. Furthermore, the well walls impede analytical probes from getting close to or contacting the sample in the wells. Still further, because these assay plates are often reused, they are cleaned or washed between uses to avoid contamination. However, complete removal of the samples from the wells is typically problematic, as it can be difficult to clean out all the wells of a well plate, especially if the wells have tight corners or contain a sample that is dried or resistant to cleaning. In this case, mechanical "scrubbing" is required and efficient and complete scrubbing is hindered by the presence of walls.

Another type of assay plate developed by the Discovery Labware business unit of BD Biosciences (Becton, Dickinson and Company) is the BD FALCON™ virtual-well plate. The BD FALCON™ virtual-well plate is used to create an array of aqueous-based liquid samples by tailoring the surface-tension properties of a substrate to achieve sample separation without the wall features, found in wells. These virtual-well plates consist of a hydrophilic substrate coated with a hydrophobic mask layer containing an array of openings or virtual-wells that are left uncoated. A sample liquid is deposited into each uncoated hydrophilic virtual-well. As each virtual-well is surrounded by the hydrophobic mask, high contact angles are created where the sample liquid contacts the mask, thereby restricting fluid transfer between the virtual-wells.

These virtual-wells work sufficiently well for aqueous-based sample liquids with high surface tensions. However, when low surface tension fluids, such as organic solvent-based fluids or surfactants containing aqueous samples, are used on these virtual-well plates, the sample liquid is not sufficiently contained within the virtual wells. This leads to adjacent drops merging with one another, thereby impairing the value of the plate.

In light of the above, there is a need for an improved assay plate that can hold multiple samples, while addressing the drawbacks of the prior art. Specifically, the assay plate should be able to define an array of distinct samples. In addition, the assay plate should be capable of being used with any type of liquid, including organic solvent-based liquids, while providing unobstructed views and/or contact with each sample thereon.

BRIEF SUMMARY OF THE INVENTION

According to the invention there is provided an assay plate. The assay plate includes a substrate having a substrate surface and at least one raised pad extending from the substrate surface. The raised pad includes a substantially planar level (0 degree angle) sample receiving surface configured for holding a sample thereon for in situ experimentation. In a preferred embodiment, the sample at least as initially applied preferably has fluid, liquid or gel properties, i.e., has a tendency to flow. The sample receiving surface preferably has at least one sharp edge at the junction between a sidewall coupling the sample receiving surface to the substrate surface. The sample receiving surface is preferably a circle, oval, square, rectangle, triangle, or any other polygon or irregular shape that is sized to hold a predetermined volume of the sample. The raised pad is preferably cylindrical.

Further according to the invention there is provided a method of using the above described assay plate. Once a raised pad extending from a substrate is formed, a sample is deposited on the raised pad. The sample preferably includes suspensions, emulsions, dispersions, gels, solutions, foams, creams, melted materials, or semi-solids with fluid, liquid, or gel like properties. The sample may contain a single component or multiple components. Non-limiting examples of components include active pharmaceutical ingredients (API), adhesives (including those appropriate for adhering medical devices, such as a transdermal patch, to the skin), enhancers used in the transport of APIs across tissue and membranes. The samples contained on the raised pads may be processed using drying, heating, cooling, freezing, vapor soaking, crystallizing, evaporation, or lyophilization processes. Experiments are subsequently performed using the sample on the raised pad before, during, and/or after the processing.

The above described apparatus contains samples within the well-defined areas created by the sharp edges (e.g. 90 degrees) of the raised pads receiving surface, thereby preventing contact with adjacent samples even in compact arrays such as a 96, 384 or 1536-sample standard assay plate format. This containment is achieved through a surface phenomenon, not by walls separating each sample.

One advantage of the assay plate is its ability to contain arrays of low-surface-tension fluids (e.g. organic solvents) without contact among adjacent samples, as well as high-surface tension fluids (e.g. water). This addresses the drawbacks associated with the prior art well and virtual-well designs. Existing virtual-well-plate designs do not work well with low-surface-tension fluids, since they are designed to contain aqueous samples. Plates with depressed wells also exhibit problems when working with organic solvent-based fluids, since these liquids tend to wet the sides of the wells due to capillary action. Another advantage is the unobstructed access to the samples the assay plate provides, since there are no walls surrounding the sample. This allows unobstructed viewing of the sample. This also allows for probes from analytical instruments to get close or even contact each sample without impedance from well walls or other geometric features (e.g., for Raman or other spectroscopy, tack and other material property testing, etc). The open access to the samples also allows for contact with biological substances, such as skin for transdermal experiments or cultured cells and tissue for permeability experiments, membranes, cultured cells, epidermal tissue, and other human and animal tissue, plant tissue such as leaves or synthetic materials, such as artificial membranes may also be used, for e.g., in permeability experiments.

The present invention further relates to systems and methods to prepare a large number of component combinations, at varying concentrations and identities, at the same time, and methods to test tissue barrier transfer of components in each combination. The methods of the present invention allow determination of the effects of additional or inactive components, such as excipients, carriers, enhancers, adhesives, and additives, on transfer of active components, such as pharmaceuticals, across tissue, such as skin or stratum corneum, lung tissue, tracheal tissue, nasal tissue, bladder tissue, placenta, vaginal tissue, rectal tissue, stomach tissue, gastrointestinal tissue, nail (finger or toe nail), eye or corneal tissue, and plant tissue (leaf, stem or root). The invention thus encompasses the testing of pharmaceutical compositions or formulations in order to determine the overall optimal composition or formulation for improved tissue transport, including without limitation, transdermal transport. Specific embodiments of this invention are described in detail below.

In one embodiment, the invention concerns an apparatus for measuring transfer of components across a tissue, comprising an assay plate with a substrate surface having raised pad sample receiving surfaces, an array of samples supported by raised pads on the assay plate, a membrane or tissue specimen overlaying the array of samples, and a reservoir plate secured to a side of the membrane or tissue specimen opposite the array of samples. In one aspect of the invention, each sample (wherein the term "sample" as used herein includes replicates) in the array contains a unique composition or formulation of components, wherein different active components or different physical states of an active component are present in one or more of the samples in the sample array.

In another aspect of the present invention, each sample of the array includes a component-in-common and at least one additional component, wherein each sample differs from at least one other sample with respect to at least one of:

(i) the identity of the additional components, (ii) the ratio of the component-in-common to the additional components, or (iii) the physical state of the component-in-common.

A "component-in-common" is a component that is present in every sample in a sample array. In one embodiment, the component-in-common is an active component, and preferably, the active component is a pharmaceutical, dietary supplement, alternative medicine or a nutraceutical. The samples may be in the form of liquids, solutions, suspensions, emulsions, solids, semi-solids, gels, foams, pastes, ointments, or triturates.

In another embodiment, the invention concerns a method of measuring tissue barrier transport of a sample, comprising:

(a) preparing an array of samples supported by raised pad sample receiving surfaces on an assay plate, having an active component and at least one additional component, wherein each sample differs from at least one other sample with respect to at least one of:

(i) the identity of the active component;

(ii) the identity of the additional components, (iii) the ratio of the active component to the additional components, or (iv) the physical state of the active component;

(b) overlaying the array of samples with a tissue specimen;

(c) securing a reservoir plate to a side of the tissue specimen opposite the array of samples, the plate having an array of reservoirs corresponding to the array of samples;

(d) filling the array of reservoirs with a reservoir medium; and (e) measuring concentration of the active component in each reservoir at one or more time points to determine transport of the active component from each sample across the tissue specimen.

In a preferred embodiment, the active component is a pharmaceutical, a dietary supplement, an alternative medicine, or a nutraceutical. In another embodiment, the tissue specimen is skin and in a more specific embodiment, the tissue specimen is stratum corneum.

In another embodiment, the invention concerns a method of analyzing or measuring flux of a sample across a tissue, comprising:

(a) preparing an array of samples supported by raised pad sample receiving surfaces on an assay plate having a component-in-common and at least one additional component, wherein each sample differs from at least one other sample with respect to at least one of:

(i) the identity of an active component;

(ii) the identity of the additional components, (iii) the ratio of the component-in-common to the additional components, or (iv) the physical state of the component-in-common;

(b) overlaying the array of samples with a tissue specimen;

(c) securing a reservoir plate to a side of the tissue specimen opposite the array of samples, the plate having an array of reservoirs corresponding to the array of samples;

(d) filling the array of reservoirs with a reservoir medium; and (e) measuring concentration of the component-in-common in each reservoir as a function of time to determine flux of the component-in-common from each sample across the tissue specimen.

BRIEF DESCRIPTION OF THE DRAWINGS

For a better understanding of the nature and objects of the invention, reference should be made to the following detailed description, taken in conjunction with the accompanying drawings, in which.

Figure 1A:
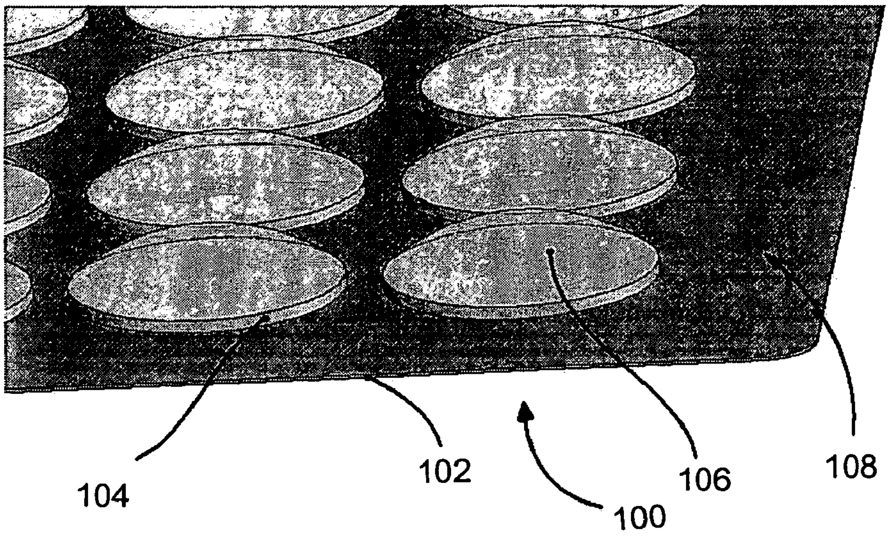
FIGS. 1A and 1B are partial oblique views of an assay plate with samples thereon, according to an embodiment of the invention.

For ease of reference, the first number of any reference numeral generally indicates the number of the figure where the reference numeral can be found. For example, 102 can be found on FIGS. 1A and 1B, and 502 can be found on FIG. 5. However, like reference numerals refer to corresponding parts throughout the several views of the drawings.

DETAILED DESCRIPTION OF THE INVENTION

The assay plate described herein is preferably used for testing (in particular High Throughput Screening on the milli-, micro-, nano-, and pico-scales) of physical, chemical, biological or biochemical properties, characteristics, or reactions. More particularly, the assay plate is used for parallel detection (including rapid detection) and monitoring of chemical or biological reactions and phenomena. Suitable uses include: transdermal formulation experiments, including measuring flux and transport of components across skin or other tissues and membranes; biological experiments; crystallization experiments, such as protein crystallization experiments, evaporative crystallization experiments, and small-molecule and protein crystallization experiments; solubility experiments; optical imaging; spectroscopy; miscibility; precipitation; mechanical testing; tactile testing; membrane/tissue permeation experiments; arrayed presentation of test articles to in vivo skin testing—where a flexible substrate is advantageous; or the like.

Figure 1B:
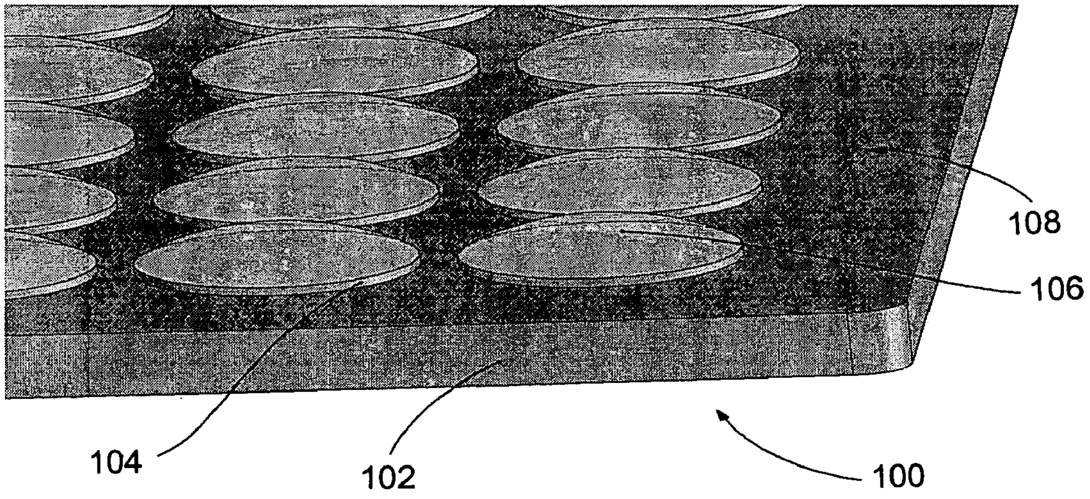

FIGS. 1A and 1B are a partial oblique view of an assay plate 100, according to an embodiment of the invention. The assay plate 100 includes a substrate 102 having a substrate surface 108. FIG. 1A exemplifies an assay plate with a thin substrate and FIG. 1B exemplifies an assay plate with a thicker substrate. The assay plate 100 also includes one or more raised pads or plateaus 104 (hereinafter "raised pad(s)") extending from the upper surface 108. Each raised pad 104 is preferably a smooth, flat and level surface configured for receiving a sample 106 thereon. Each sample 106 forms a drop on each raised pad 104 as described below in relation to FIG. 2. Once in place on top of the raised pad, the samples 106 are used for in situ experimentation. In other words, experimentation is performed while the samples are in place on the raised pads. For example, the sample 106 on each raised pad 104 may be used in an in situ transdermal formulation experiment, as described below in relation to FIG. 6.

Figure 2:
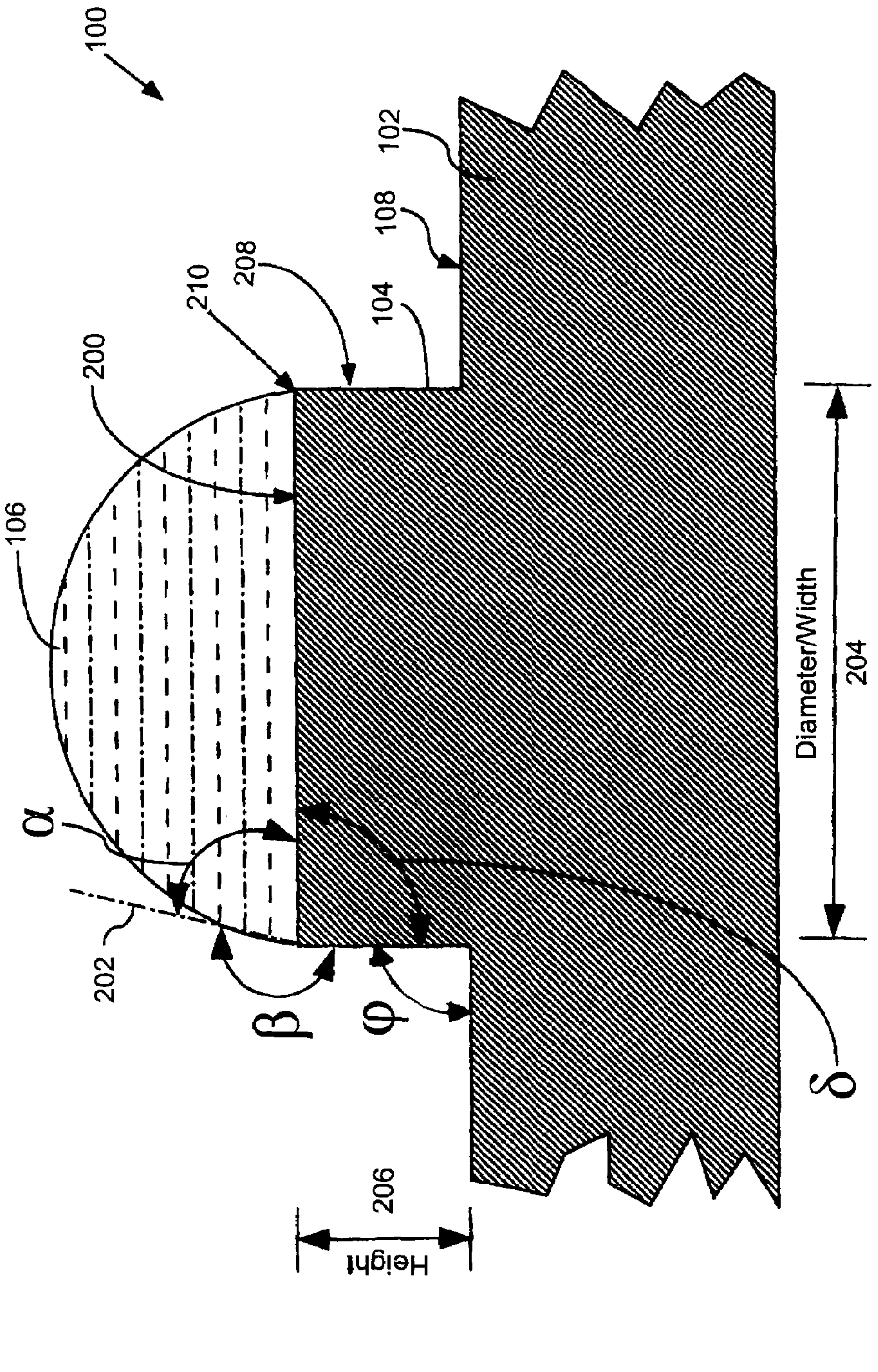
FIG. 2 is a partial cross-sectional view of the assay plate shown in FIGS. 1A and 1B containing a sample volume between sharp edge boundaries.

FIG. 2 is a partial cross-sectional view of the assay plate 100 shown in FIGS. 1A and 1B. As shown, the substrate surface 108 of the substrate 102 is preferably substantially flat or planar. By "substantially planar" it is meant essentially, basically, or fundamentally planar, but not necessarily exactly planar. The substrate 108 may comprise concave areas or cavities such as a well. The substrate may consist of both flat and concave areas or consist of only a flat or concave surface. The substrate 102 and/or raised pads 104 can be made of any suitable material, such as metal, glass, ceramic, or plastic. Suitable materials are preferably compatible with the sample 106 being used. For example, the material should be resistant to corrosion by the sample. Suitable materials are also preferably chosen for their low cost and ease of manufacture. Examples of suitable materials include stainless steel, titanium, aluminum, glass, polystyrene, polypropylene, or the like. In one embodiment, the assay plate 100 is injection-molded or cast to generate large quantities of assay plates, each at a low per unit cost.

If required, the material may be chosen for its optical properties. This is especially useful where optical inspection of the samples occurs using techniques like video, photography, microscopy, fluorescence, or the like. In this embodiment, an optically transparent array plate is positioned between a light source and a detector. Examples of suitable optically transparent materials include various glasses and/or plastics and/or minerals such as quartz. Transparent raised surface plates made of glass, plastic, and quartz have been used in crystallization studies and other experiments which rely on the transparency of the substrate such as spectroscopic analysis, particle size measurement, and opacity determination. The samples contained on clear raised surface plates are imaged using microscopy, cameras, lasers, and other optical probes and sensors. The samples are imaged to detect the presence of precipitates, crystals, contaminants, immiscible boundaries, inclusions, topology, and other visual features. Of particular interest is detecting the nucleation and growth of crystalline material within samples on the plates over time. Imaging is done preferably using the transmission of white light, cross-polarized light, or monochromatic light through the clear plate or by other appropriate means, such as reflective illumination.

Moreover, the raised pads 104 are preferably an integral part of the substrate 102. For example, a block of material is machined or etched, either chemically or physically, to form the raised pads 104 on the substrate 102. Alternatively, the raised pads 104 may be formed concurrently with the substrate, such as by using an injection molding, casting or embossing technique. Further, the substrate with raised pads may be further supported by securing it to a base plate or a number of base plates. This could for example, reduce manufacturing costs if the subtrate with raised pads is made from an expensive material. The subtrate plate with raised pads could be made with a low height or profile (e.g., about 250 microns total height with each raised pad extending about 200 microns from a substrate of about 50 microns in height), e.g., made from a thin block of material, and then supported by securing it to an underlying base plate made of a less expensive material. It may also be easier to manufacture a substrate plate with raised pads having a low height.

Each raised pad 104 includes a substantially planar sample receiving surface 200. Each raised pad is preferably parallel to the substrate surface 108 or level or horizontal. Each raised pad 104 also preferably includes one or more sidewalls 208 that extend from the substrate surface 108 to the sample receiving surface 200. Each sidewall 208 is preferably orthogonal to the substrate surface (e.g., $\phi$=90 degrees) 108 or slightly undercut ($\phi$<90 degrees). Each sidewall 208 is also preferably orthogonal to the sample receiving surface 200 (e.g., $\delta$=90 degrees) or slightly undercut ($\delta$<90 degrees).

Figure 4A:
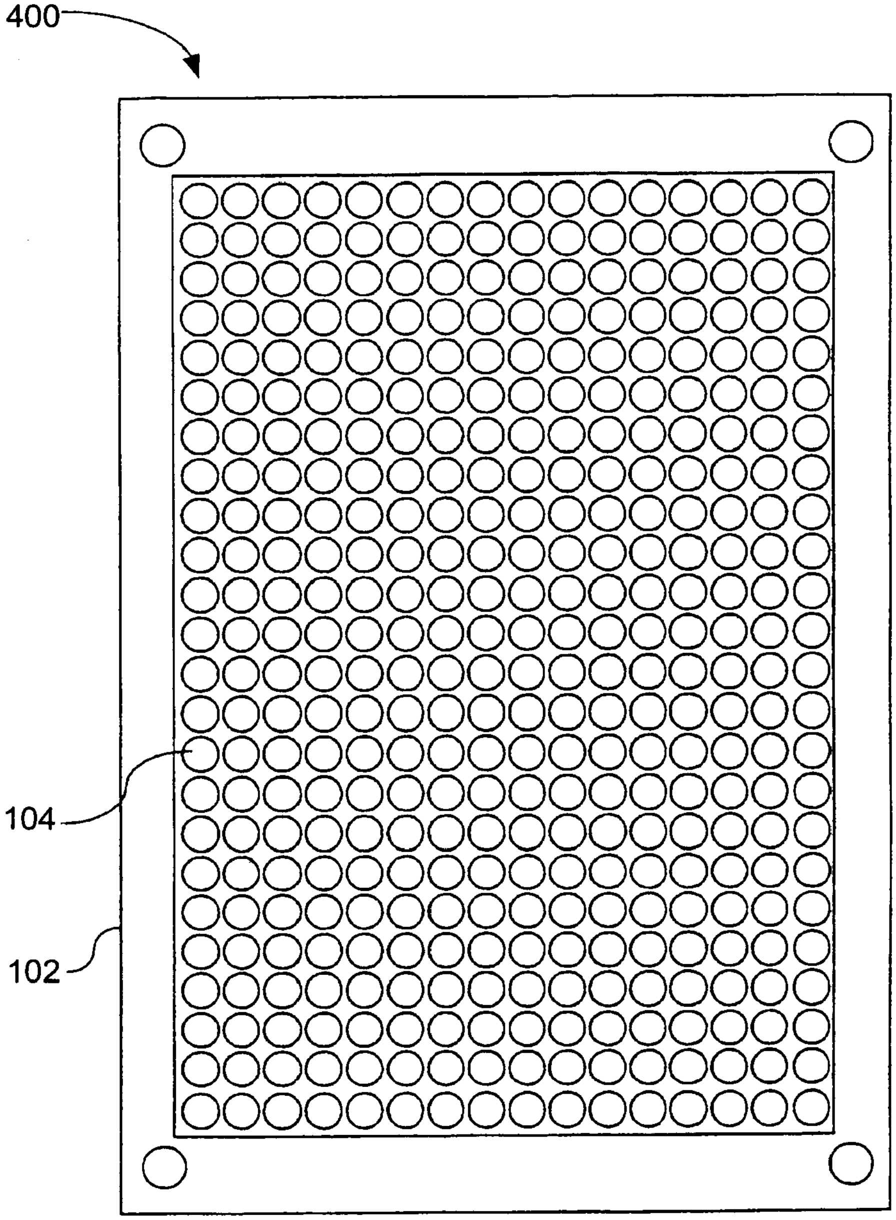
FIG. 4A is a top view of an assay plate, according to yet another embodiment of the invention.

In addition, the sample receiving surface 200 preferably has one or more sharp corners or edges 210 at the junction between the sidewall 208 and the sample receiving surface. By sharp it is meant that the junction between the sample receiving surface 200 and the sidewall 208 has substantially no radius, or a small radius dictated by the method of manufacture, typically less than 0.002 inches. The sample receiving surface 200 may have any suitable shape, such as a circle, as shown in FIGS. 1 and 4A, square, oval, rectangle, triangle, pentagon, hexagon, octagon, or any other polygon, regular or irregular shape. In addition, the shape of the sample receiving surface 200 can be chosen to hold a predetermined volume of sample. The area/shape is chosen for the type of experiment and the amount of volume the pads need to hold. The maximum volume contained by a circular pad (if the maximum contact angle is 90 degrees) is estimated by the equation for a half-sphere with a cross-sectional area of pi*(diameter/2)$^2$ and volume of ⅔·pi·r$^3$ If the range of diameters is taken as 50 μm to 1 cm, then the areas are in the range of 2E-5 cm$^2$ to 0.8 cm$^2$ and maximum volumes of ~33 picoliters to ~300 microliters. Examples of raised pad diameter ranges of the present invention are about 50-100 μm, 100-200 μm, 200-300 μm, 300-400 μm 400-500 μm, 500-600 μm, 600-700 μm, 700-800 μm, 800-900 μm, 900 μm-1 mm, 1 mm-2.5 mm, 2.5 mm-5 mm, 5 mm-7.5 mm, 7.5 mm-1 cm, 1 mm-9 mm, 1 mm-5 mm, 5 mm-1 cm or 1 cm-2 cm. Examples of sample volume ranges included in the present invention are about 30 picoliters-100 picoliters, 100-250 picoliters, 250-500 picoliters, 500-750 picoliters, 750 picoliters-1 nL, 1 nL-10 nL, 10 nL-50 nL, 50 nL-100 nL, 100 nL-200 nL, 200 nL-300 nL, 300 nL-400 nL, 400 nL-500 nL, 500 nL-600 nL, 600 nL-700 nL, 700 nL-800 nL, 800 nL-900 nL, 900 nL-1 μl, 1 μl-5 μl, 5 μl-10 μl, 10 μl-50 μl, 50 μl-100 μl, 100 μl-150 μl, 150 μl-200 μl, 200 μl-250 μl, 250 μl-300 μl. The pads may be arranged in either an ordered (regularly spaced) or unordered manner. The pads may be arrayed in a single row or in multiple rows. In the preferred embodiment, the pads are arrayed in an ordered manner and the size of the surface is also chosen to fit into a standard microplate format. For example, for an assay plate having 96 raised pads, one is restricted to about a 9 mm center-to-center spacing and a diameter of each raised pad of between about 1 to about 8.5 mm; for an assay plate having 384 raised pads, one is restricted to about a 4.5 mm center-to-center spacing and a diameter of each raised pad of between about 0.5 to about 4.2 mm; for an assay plate having 1536 raised pads, one is restricted to about a 2.25 mm center-to-center spacing and a diameter of each raised pad of between about 0.05 to about 2 mm.

In light of the above, a preferred assay plate having 1536 raised pads will have about 16 raised pads per cm$^2$, thereby having raised pads with diameters of between 50 μm to 2 mm, each holding liquid volumes of 33 picoliters to 2 μl per pad. Also, the pitch or distance between raised pads is preferably about 0.225 cm.

Another preferred assay plate having 384 raised pads will have about 4 raised pads per cm$^2$, thereby having raised pads with diameters between 0.5 and 4.2 mm, each holding liquid volumes of 32 nL to 20 μL per pad. Also the pitch or distance between the raised pads is preferably about 0.45 cm. Included in the invention are assay plates with at least 10, 50, 150, 200, 250, 300, 400, 500, 600, 700, 800, 900, 1000, 1100, 1200, 1300, 1400, 1500, 1600, 2000, 2500, 3000, 4000, 5000, or 6000 pads.

The purpose of the raised plateaus or pads with sharp edges is to confine samples to the top of the raised pads, as described below. In this way, discrete samples may be confined to specific positions on the assay plate. The height of the raised pads (the distance between the substrate surface and the top or edge of the pad) is generally, but not limited to, about 50 μm to about 10 mm, or more specifically, about 50 μm to about 5 mm, about 50 μm to about 1 mm, about 500 μm to about 5 mm, about 500 μm to about 1 mm, about 100 μm to about 300 μm, about 150 μm to about 250 μm, or about 200 μm. For glass, quartz and other materials that are etched, e.g. sand blasted, the raised pads may be specified as a minimum height with varying maximum heights due to variations in the etching procedure.

The height of the substrate surface or thickness of the substrate may vary considerably. The substrate may be very thin, particularly if supported by a base plate, or thick, particularly if not substrate further supported by a base plate. Generally, the height of the substrate surface is normally but not limited to 10 μm to about 2 cm. If a base plate is used, the height of the substrate surface may be for example about 10 μm to about 5 mm, about 10 μm to about 1 mm, about 10 μm to about 500 μm, about 100 μm to about 250 μm, 10 μm to about 100 μm, about 500 μm-1 mm, about 1 mm-5 mm, about 5 mm-1 cm, or about 1 cm-2 cm. The height of the substrate surface or base plate will depend, in part, on the desired rigidity and the rigidity of the material used and the specifications of instrumentation that handles the plates.

In one aspect of the present invention, the substrate plate is pliable or flexible for direct application to live skin in situ. This aspect includes methods comprising adhering or otherwise securing (e.g., straps or fasteners) a substrate plate with raised pads and an array of samples to the skin of a live host animal, e.g., rodent (e.g., mouse, rat, etc), bird, dog, horse, cow, pig, goat, rabbit, primate (monkey or ape and including humans) or cat. After a period of time, the plate can be removed and a parameter quantified or qualified. For example, one could measure relative amount of irritation or other biological responses caused by the samples with different components by measuring the degree of wheel and flare, infiltration of white blood cells, or other cellular responses. One could also biopsy the skin for transfer of sample components across the skin or for measuring other cellular response factors such as release of cytokines.

Figure 3:
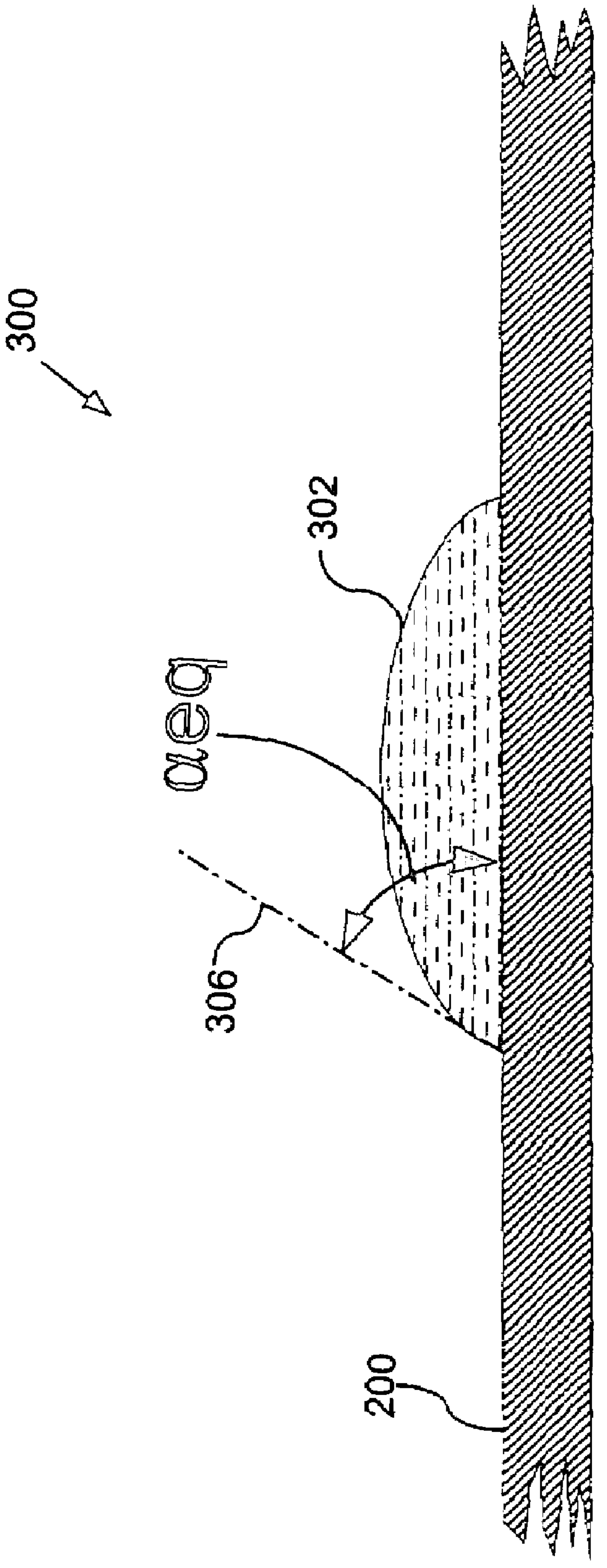
FIG. 3 is a partial cross-sectional view of a small liquid drop on a sample receiving surface away from any sharp edge boundaries.

FIG. 3 is a partial cross-sectional view 300 of a small liquid drop 302 on a sample receiving surface 200. Normally, a volume of liquid 302 that is deposited onto a smooth continuous surface spreads until it reaches an equilibrium state. In this state, a contact angle between the liquid 302 and the surface is called the equilibrium contact angle ($\alpha_{eq}$). If the equilibrium contact angle ($\alpha_{eq}$) is high, drops of liquid bead up on the surface of the substrate 304. If the angle is low, the drops spread out farther, and when they are positioned in tight arrays, easily merge with one another.

The equilibrium contact angle ($\alpha_{eq}$) depends on the material properties of the surface and the sample, specifically, the relative surface energies ($\gamma$) of the system.

The change in the surface free energy, $\Delta G^s$, accompanying a small outward displacement of a liquid on a surface to cover additional solid surface of area $\Delta A$, is $$\Delta G^s = \Delta A(\gamma_{SL} - \gamma_{SV}) + \Delta A \gamma_{LV} \cos(\alpha - \Delta\alpha) \quad (1)$$

where S denotes the solid, L denotes the liquid phase, V denotes the vapor phase, and the angles filled by the solid, liquid and vapor by $\delta$, $\alpha$, and $\beta$ respectively.

At equilibrium, $$\lim_{\Delta A \to 0}(\Delta G^S/\Delta A)=0 \quad (2)$$

This gives Young's equation which describes the equilibrium contact angle, $$\gamma_{SL}-\gamma_{SV}+\gamma_{LV}\cos\alpha=0 \quad (3)^1$$

or, $$\alpha=\alpha_{eq}=\cos^{-1}[(\gamma_{SV}-\gamma_{SL})/\gamma_{LV}] \quad (4)$$

Therefore, the equilibrium contact angle for a smooth continuous solid surface is described by the surface tension properties of the system. The above formula describes the statics for very small volumes of liquid placed onto the center of a raised pad 104.

If, however, the volume of the liquid is large enough to spread to the edge of the raised pad or plateau 104, a surface discontinuity, the condition of equilibrium is given by "Gibbs's inequalities" (see FIG. 2):

$$\gamma_{LV}\cos\alpha \leqq \gamma_{SV}-\gamma_{SL} \text{ and } \gamma_{LV}\,\mathrm{COS}\,\beta \leqq \gamma_{SL}-\gamma_{SV} \quad (5)^2$$

Since $\gamma_{LV}>0$, Gibbs inequalities become:

$$\alpha \leqq \alpha_{eq}, \text{ and } \beta \leqq \pi-\alpha_{eq} \quad (6)^2$$

Since $\delta+\alpha+\beta=2\pi$, $$\alpha_{eq} \leqq \alpha \leqq (\pi-\delta)+\alpha_{eq} \quad (7)^2$$

where $(\pi-\delta)$ is a term dictated by the geometry of the surface, and $\alpha_{eq}$ is given by the surface properties of the system as given in equation 4.

Support for formula 3 can be found in Adamson, A. W, and Gast, A. P *Physical Chemistry of Surfaces* sixth addition, John Wiley and Sons, Inc. NY, 1997 pg. 353, while support for formulae 5,6, and 7 can be found in Dyson, D. C Contact line stability at edges: Comments on Gibbs Inequalities Phys. Fluids 31 (2), February 1988 pp. 229-232, both of which are incorporated herein by reference.

Liquid dispensed onto a solid surface with an ideally sharp edge will spread to the edge and assume a contact angle up to a theoretical maximum of $(\pi-\delta)+\alpha_{eq}$. For a raised plateau geometry with vertical walls, the contact angle can be at most $\alpha_{eq}+90°$.

In a preferred embodiment, each raised pad 104 has a height 206 of greater than 10 μm but less than 1 cm and an average diameter or width 204 of between 100 μm and 10 mm. More specifically, a preferred embodiment includes raised pads, where each raised pad 104 has a height between 200 μm and 1 mm and a diameter of between 500 μm and 8 mm. Also in a preferred embodiment, the diameter 204 is larger than the height, and the angle (δ) between the sample receiving surface 200 and the sidewall 208 is preferably less than or equal to 90 degrees. (See FIG. 5 for an alternative embodiment). The preferred number of pads per plate for the high throughput assay plate is equal to or greater than 12, 24, 96, 384, or 1536. Included in the invention are assay plates with at least 10, 50, 150, 200, 250, 300, 400, 500, 600, 700, 800, 900, 1000, 1100, 1200, 1300, 1400, 1500, 1600, 2000, 2500, 3000, 4000, 5000 or 6000 pads. The preferred distance between adjacent pads is between 0.05 mm-10 mm, 0.1 mm-5 mm, 0.1-1 mm, 0.25-0.75 mm, 0.25-1 mm, 0.5 mm-1 mm, 0.1 mm-0.5 mm, 0.25-0.5 mm, 0.4-0.55 mm, and about 0.45-0.5 mm. The preferred angle of the pad at the sharp edge is between 45 and 135 degrees, more particularly 75 and 120, more preferred 75 and 90, and a particularly preferred angle is 90 degrees. However, this angle can vary and the surface phenomena will still function to contain the sample, as long as there is a surface discontinuity.

Fluids with low surface energies such as many organic solvents tend to have small equilibrium contact angles, and tend to spread out on many conventional surfaces such as glass, metal, and plastic surfaces. Accordingly, the raised surface geometry of the invention allows the contact angle of the liquid to be increased at the edges of the plateaus. This allows for a greater volume of liquid to be confined to a smaller area, thereby allowing for higher density sample arrays.

The raised surface substrate described above addresses the drawbacks of containing low surface-tension fluids by using surface discontinuities, such as sharp edges. These surface discontinuities help generate non-equilibrium contact angles to contain the sample regardless of the sample's surface tension properties.

Figure 4B:
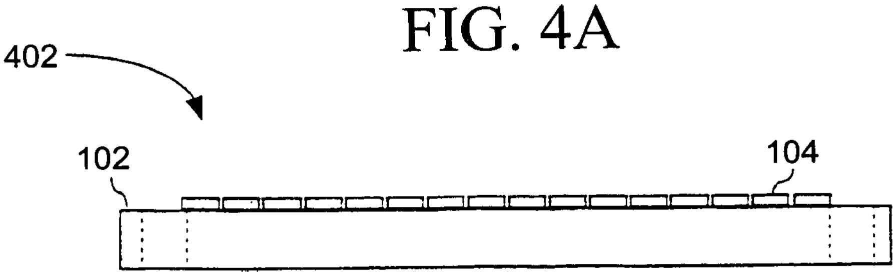
FIG. 4B is a side view of the assay plate shown in FIG. 4A.

FIG. 4A is a top view 400 and FIG. 4B is a side view 402 of an assay plate, according to another embodiment of the invention. The embodiment shown includes a standard sample array having 384 sample receiving surfaces. Alternatively, any other array (industry standard or non/standard) may be used, such as an array having 96 or 1536 sample receiving surfaces. In an embodiment of an array having 384 sample receiving surfaces, the diameter 204 (FIG. 2) of each raised pad is approximately 4 mm.

In an alternative embodiment, a plate with 1536 pads distributed in a regular array over the same plate area would have a diameter of approximately 1.8 mm. These diameters are chosen to maintain at least 200 μm, and preferably approximately a 200 to 500 μm distance between adjacent pads to prohibit two adjacent drops from touching as well as for ease of manufacture. Also in an alternative embodiment, the assay plate may form part of a sealed or closed system.

As discussed above, the assay plate may be the size of a standard microtiter plate. In other embodiments, the dimensions of the assay plate are less than about 55 cm×35 cm, 40 cm×28 cm, 27 cm×18 cm, 13 cm×9 cm, or 7 cm×5 cm, or is about 12.7 cm×8.5 cm. In other embodiments the dimensions of the assay plate are greater than about 3 cm×2 cm, 6 cm×4 cm, 12 cm×8 cm, 24 cm×16 cm, 48 cm×32 cm or greater than about 60 cm×40 cm.

Figure 5:
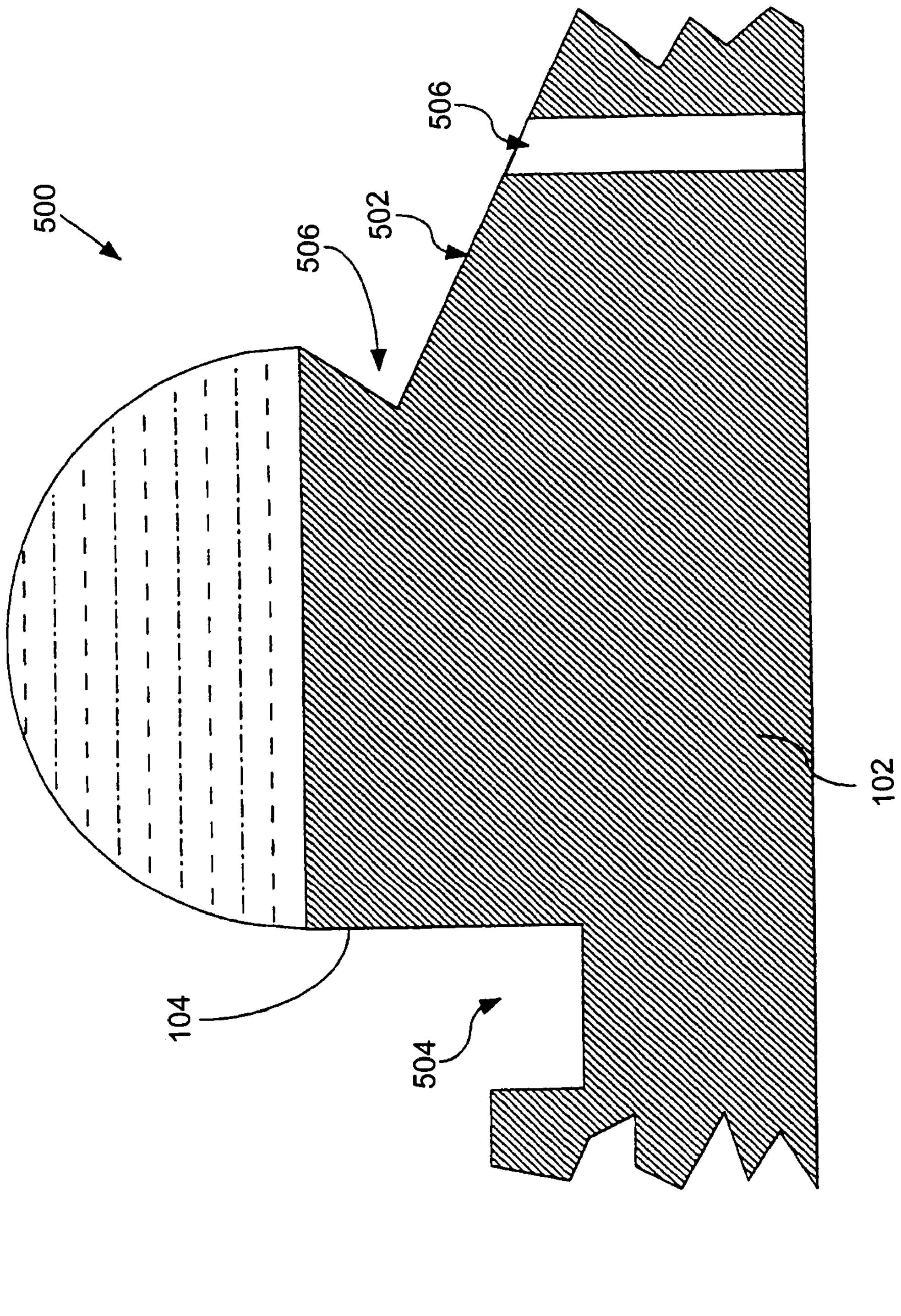
FIG. 5 is a partial cross-sectional view of an assay plate, according to still another embodiment of the invention.

FIG. 5 is a partial cross-sectional view of an assay plate 500, according to other embodiments of the invention. Assay plate 500 includes a substrate 102, having substrate surfaces different to that shown in FIG. 2. FIG. 5 illustrates multiple alternative embodiments of the present invention. Each of the embodiments of FIG. 5 are independent embodiments. Any one or any combination of one or more of the embodiments may be included or excluded from the present invention. For example, the substrate surface may be sloped 502 so that any excess sample that falls from the raised pad 104 drains from the substrate surface. Alternatively, the substrate surface may include one or more cavities 504 for collecting excess sample that falls from the raised pad 104, or for containing another fluid used to react with the sample on the raised pad 104. Such cavities 504 are particularly useful for sitting-drop type experiments.

Similarly, the assay plate 500 can be engineered to utilize the interstices between the raised pads 104 to deposit another fluid used to interact with the samples deposited onto the raised pads. Furthermore, holes 506 can also be provided in the interstices or channels between raised pads to provide drainage of liquids that may have spilled from the raised pads, to introduce (or evacuate) vapors, gases, or liquid reactants that may interact with the components dispensed onto the raised pads, or to create a vacuum between the assay plate and the sample (e.g., tissue or membrane) overlaying the assay plate. In another embodiment, holes are provided in the raised pads to provide for dispensing or removing a sample from the surface of the raised pads. Holes may also be provided in the raised pads to introduce or remove gases or liquids from the plate. The channels between the raised plateaus can also be filled with a secondary fluid if desired, so long as the fluid does not fill to the top of the raised pads.

The raised pad 104 may also include an undercut 506, i.e., having an angle (δ) between the sample receiving surface and the sidewall of less than 90°. This undercut is advantageous if more volume of a secondary fluid in the cavity between pads is desired.

In addition, the raised-pad arrays can also be created in irregular arrangements, with pads of varying sizes grouped as needed by the experiment. For example, groups of larger and smaller pads could be formed to perform experiments where different samples on the various raised pads interact or react with one another. This embodiment is also well suited to sitting-drop, or vapor diffusion and crystallization, experiments.

Figure 6:
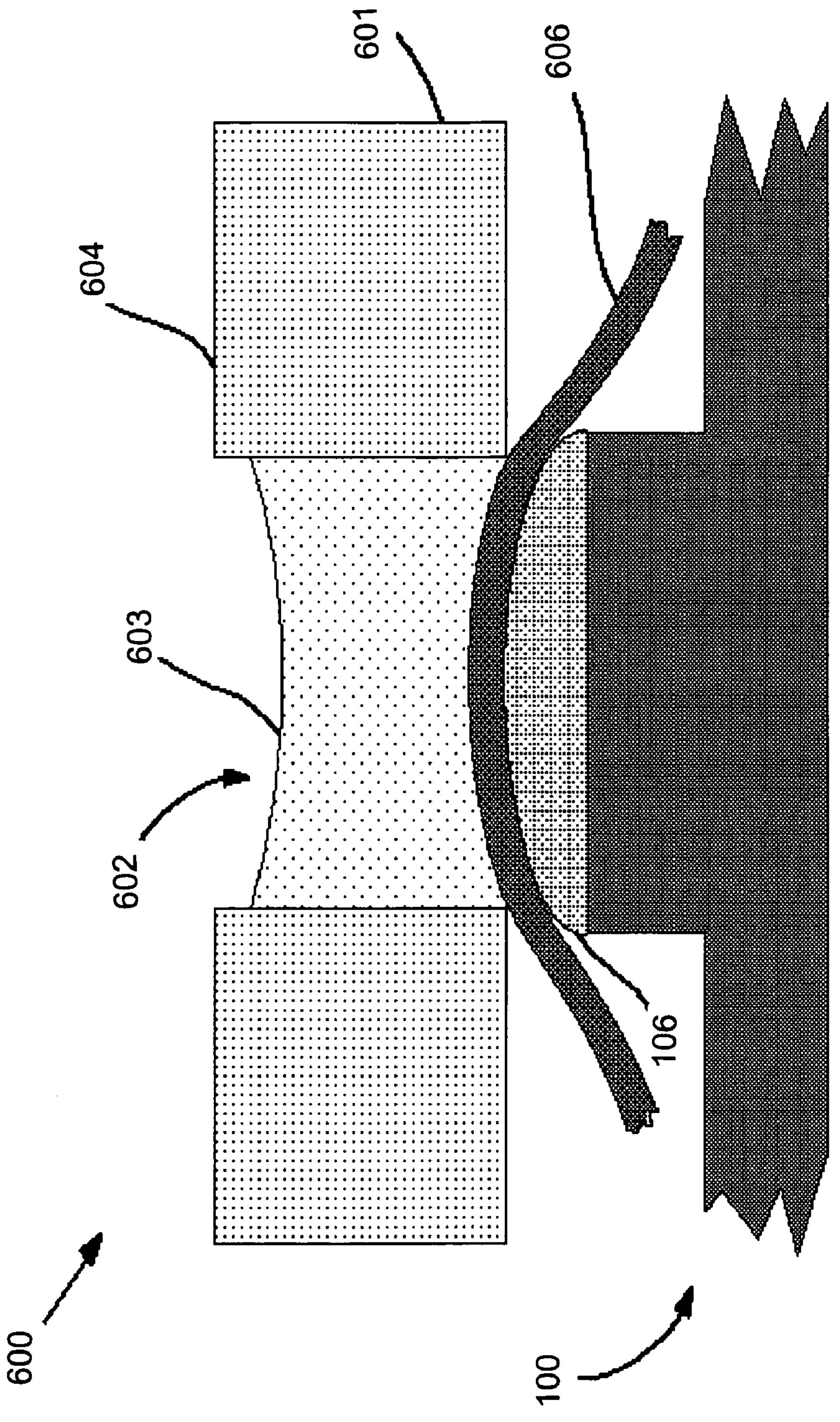
FIG. 6 is a partial cross-sectional view of the assay plate shown in FIG. 2 being used in a transdermal formulation experiment.

FIG. 6 is a partial cross-sectional view of the assay system shown in FIG. 2 being used in a transdermal formulation experiment. This embodiment shows an exemplary use of the assay plate 100 shown and described in relation to FIG. 2. The transdermal formulation experiment is undertaken to ascertain the transdermal delivery of a chemical contained in the sample through a layer of skin or tissue. Tissue specimen 606 overlays sample 106 on a raised surface assay plate 100. Reservoir plate 600 is secured to tissue specimen opposite the sample. Reservoir plate contains holes that form wells 602 with sidewalls 601. The solid material between wells has a top surface 604. Reservoir medium 603 is added to wells once reservoir plate is secured to tissue sample.

The screening systems and methods of the present invention may be used to identify optimal compositions or formulations to achieve a desired result for such compositions or formulations, including without limitation, construction of a transdermal delivery device. In particular, the systems and methods of the present invention may be used to identify 1) optimal compositions or formulations comprising one or more active components and one or more inactive components for achieving desired characteristics for such compositions or formulations, 2) optimal adhesive/enhancer/additive compositions for compatibility with a drug, 3) optimal drug/adhesive/enhancer/additive compositions for maximum drug flux through stratum corneum, and 4) optimal drug/adhesive/enhancer/additive composition to minimize cytotoxicity.

The methods of the present invention can be performed using various forms of samples. Typically, the methods are performed either with liquid samples or with solid or semi-solid samples.

As used herein, "liquid source" means that the sample containing the component or components being measured or analyzed is in the form of a liquid, which includes, without limitation, liquids, solutions, emulsions, suspensions, and any of the foregoing having solid particulates dispersed therein.

As used herein, "solid source" means that the sample containing the component or components being measured or analyzed is in the form of a solid or semi-solid, which includes, without limitation, triturates, gels, films, foams, pastes, ointments, adhesives, high viscoelastic liquids, high viscoelastic liquids having solid particulates dispersed therein, and transdermal patches.

As used herein, "liquid" refers to the state of matter in which a substance exhibits a characteristic readiness to flow, little or no tendency to disperse, and relatively high incompressibility. Matter or a specific body of matter in this state.

As used herein, "solid" refers to a substance having a definite shape and volume; one that is neither liquid or gaseous.

As used herein, "semisolid" refers to a substance having properties partly of that of a solid and partly that of a liquid.

As used herein, "semisolid" refers to a substance having properties partly of that of a solid and partly that of a liquid.

As used herein, "solution" refers to a chemically homogenous mixture of two or more substances all dissolved together.

As used herein, "gel" refers to a usually translucent, non-greasy emulsion or suspension semisolid. Usually containing a gelling agent in quantities sufficient to impart a three-dimensional, cross-linked matrix. Usually hydrophilic, and contains sufficient quantities of a gelling agent such as starch, cellulose derivatives, carbomers, magnesium, aluminum silicates, xanthan gum, colloidal silica, aluminum or zinc soaps.

As used herein, "Emulsion" refers to a suspension of small volumes of one liquid in a second liquid with which the first will not mix.

As used herein, "Suspension" refers to a mixture in which fine particles are suspended in a fluid where they are supported by buoyancy or are sterically hindered from interacting with one another and thus stay separated in space.

As used herein, "Ointment" refers to an opaque or translucent, viscous, greasy emulsion or suspension semisolid which generally contains a >50% of a hydrocarbon-based or a polyethylene glycol-based vehicle and <20% of volatiles. Thick, translucent or opaque: holds a stiff peak when a drop is placed on a flat surface. Usually lipophilic, 20% of volatiles as measured by LOD (loss on drying).

As used herein, "cream" refers to an opaque, viscous, non-greasy to mildly greasy emulsion or suspension semisolid which contains <50% of hydrocarbons or polyethylene glycols as the vehicle and/or >20% of volatiles. There are two types of creams: a hydrophilic cream with water as the continuous phase and a lipophilic cream with oil as the continuous phase. A cream is thick, opaque: holds a soft to stiff peak when a drop is placed on a flat surface. Hydrohilic creams have water (the aqeous phase) as the continuous phase. Lipophilic creams have oil (the lipophilic phase) as the continuous phase.

As used herein, "paste" refers to an opaque, viscous, greasy to mildly greasy semi-solid dosage form for external application to the skin, which contains a large proportion (i.e. 20-50%) of solids finely dispersed in an aqueous or fatty vehicle. Pastes are very thick, opaque; holding a stiff peak when placed on a flat surface. Containing a large proportion (20-50%) of dispersed solids in a fatty or aqueous vehicle.

As used herein, "foam" refers to a mass of bubbles of air or gas in a matrix of liquid film, especially an accumulation of fine, frothy bubbles form in or on the surface of a liquid, as from agitation or fermentation.

As used herein, "triturate" refers to a mixture that has been crushed and mixed thoroughly by rubbing or grinding.

As used herein, "viscoelastic liquids" refers to liquids displaying viscoelastic properties, i.e. having viscous as well as elastic properties.

As used herein, "reservoir medium" refers to a liquid, solution, gel, or sponge that is chemically compatible with the components in a sample and the tissue being used in an apparatus or method of the present invention. In one embodiment of the present invention, the reservoir medium comprises part of the specimen taken to measure or analyze the transfer, flux, or diffusion of a component across a tissue barrier. Preferably, the reservoir medium is a liquid or solution.

As used herein, the terms "array" or "sample array" mean a plurality of samples associated under a common experiment, wherein each of the samples may comprise one or at least two, three, four, or more components, and where at least one of the components may be an active component. In one embodiment of the present invention, one of the sample components is a "component-in-common", which as used herein, means a component that is present in every sample of the array, with the exception of negative controls. The term "sample" includes replicates, e.g. where n=2, 3, 4, 5, 6, or more.

In one aspect of the present invention directed to measuring transfer or flux across a tissue, a sheet of tissue specimen is placed over an array of samples (wherein the samples are placed on the raised pad sample receiving surfaces of the assay plate) in a manner which avoids formation of air pockets between the tissue specimen and the sample. In a preferred embodiment, the sample is first dried or partially dried. Alternatively, the sample is dried, additional sample added, and dried again until a sufficient amount of sample remains on the raised pad. Multiple samples may also be layered on the pad surface. In one embodiment, each layer is dried before the next layer is added.

The tissue is preferably a sheet of tissue, such as skin, lung, tracheal, nasal, placental, vaginal, rectal, colon, gut, stomach, bladder, or corneal tissue. Plant tissue is also included in the present invention including leaf, stem and root tissue. Synthetic tissue and membranes are also included in the present invention. Preferably, tissue is skin tissue or stratum corneum. If human cadaver skin is to be used for tissue, one known method of preparing the tissue specimen entails heat stripping by keeping it in water at 60° C. for two minutes followed by the removal of the epidermis, and storage at 4° C. in a humidified chamber. A piece of epidermis is taken out from the chamber prior to the experiments and placed over the substrate plate. Tissue can optionally be supported by Nylon mesh (Terko Inc.) to avoid any damage and to mimic the fact that the skin in vivo is supported by mechanically strong dermis. Alternatively, other types of tissues may be used, including living tissue explants, animal tissue (e.g. rodent, bovine or swine) or engineered tissue-equivalents. Examples of a suitable engineered tissues include DERMAGRAFT (Advanced Tissue Sciences, Inc.) and those taught in U.S. Pat. No. 5,266,480, which is incorporated herein by reference.

In an alternative embodiment of the present invention, tissue specimen is divided into a number of segments by cuts between sample wells to prevent lateral diffusion through tissue specimen between adjacent samples. Cuts may be made in any number of ways, including mechanical scribing or cutting, laser cutting, or crimping (e.g., between plates and or by using a "waffle iron" type embossing tool). Preferably, laser scribing is used as it avoids mechanical pressure from a cutting tool which can cause distortion and damage to tissue specimen. Laser cuts are performed with very small kerfs which permit a relatively high density of samples and a more efficient tissue specimen utilization. Laser tools are available that produce a minimal heat affected zone, thereby reducing damage to tissue specimen.

Figure 7:
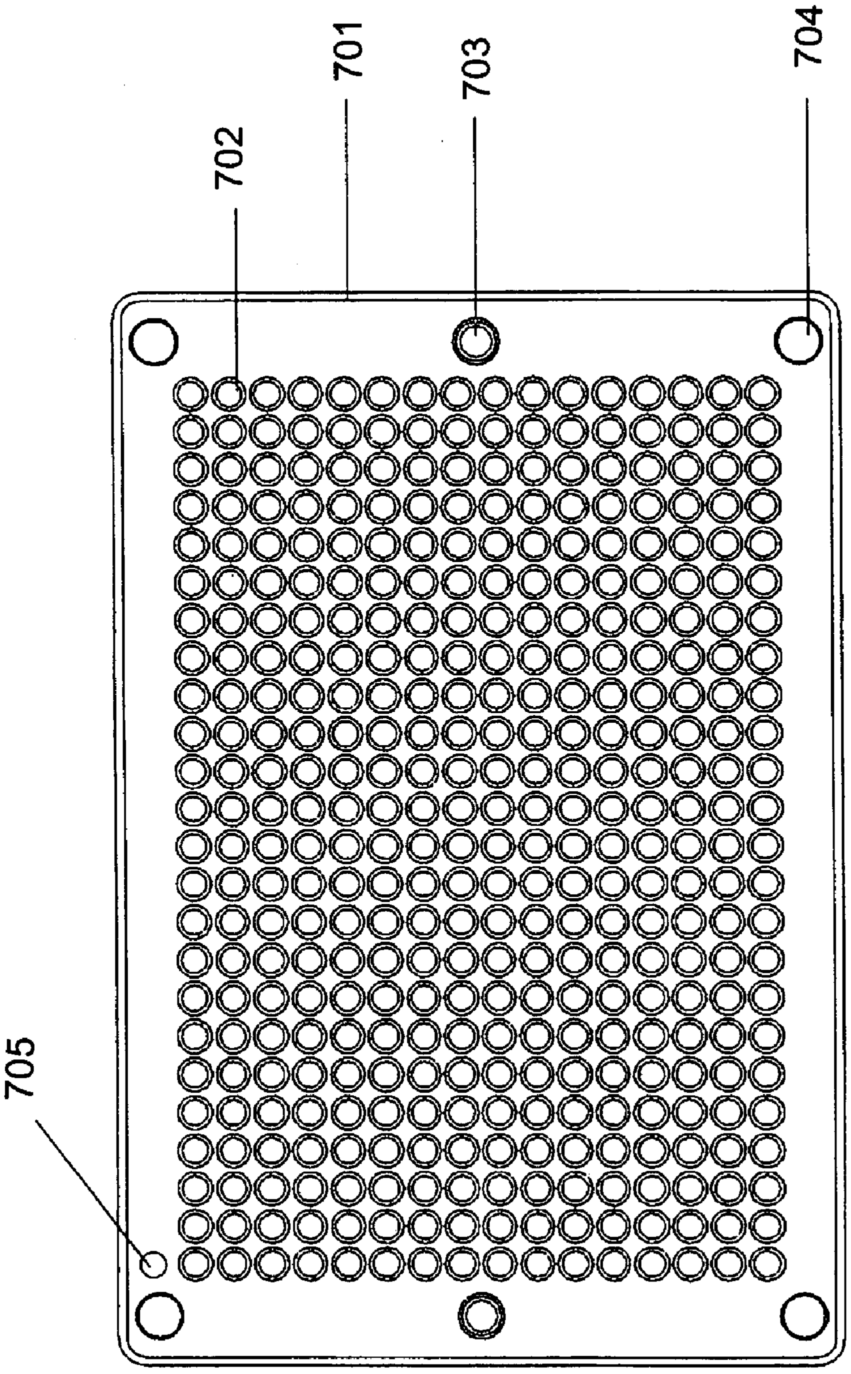
FIG. 7 is a top view of a reservoir plate. The reservoir plate is a plate with holes passing through that align with the raised pads on the assay, or substrate, plate. The reservoir plate is placed on top of tissue, on a side of tissue opposite assay plate. When reservoir plate is secured in place, the holes of the reservoir plate align over the raised pad sample receiving surfaces such that tissue separates each raised pad from holes in the receiving plate. The exemplified plate in FIG. 7 is a 384 hole reservoir plate.

A member defining one or more reservoirs therein called a reservoir plate, FIG. 7, is placed over the tissue or skin specimen. Each reservoir preferably has an opening with a diameter similar or smaller to that of the diameter of the sample on the raised pad. A smaller diameter may be advantageous in creating a seal between the top plate and the tissue specimen below, and, thus, help retain a fluid medium in the reservoir.

The reservoir plate 701, FIG. 7, is a plate with holes 702 passing through the plate that align with the raised pads on the assay plate. Normally, but not required, the number of holes is equal to the number of raised pads. The reservoir plate may further comprise a hole(s) for guide pins 703 and a hole(s), for securing the reservoir plate to the substrate and base plate 704, and an additional hole(s) for an orientation pin(s) 705. Alternatively, pins may extend from the reservoir plate for securing a substrate plate with corresponding holes. Other means for aligning the reservoir plate may also be used. The reservoir plate is placed on top of tissue, on a side of tissue opposite substrate plate. When reservoir plate is secured in place, the holes of the reservoir plate align over the raised pad sample receiving surfaces such that tissue separates each raised pad from holes in the receiving plate. The reservoir plate secures to substrate plate using clamps, screws, fasteners, magnets or any other suitable attachment means. Plates preferably secure together with sufficient pressure so as to create a liquid tight seal between the tissue and reservoir plate side facing the tissue, thus recreating a reservoirs or wells which are aligned on top of the raised pad sample receiving surfaces. Each reservoir is filled with a reservoir medium, such as a saline solution, to receive sample components or compounds that diffuse across tissue to reservoir. In one embodiment, the reservoir medium is approximately 2% BSA solution in PBS.

After the fluid medium is added to the reservoir, at an appropriate time, or multiple time intervals, a volume of the fluid medium is withdrawn from the reservoir(s) and used to measure the transfer of the chemical in the sample across the tissue specimen. In addition, water may be added to interstitial channels between the raised pads to help maintain skin hydration during the experiment. The raised pads may serve as addressable electrodes by attaching electrodes to the pads and covering a portion or all of the remaining portions of the plate with insulator material. In one embodiment of the present invention, a lid is placed on top of the reservoir plate to impede evaporation of reservoir medium.

Figure 8A:
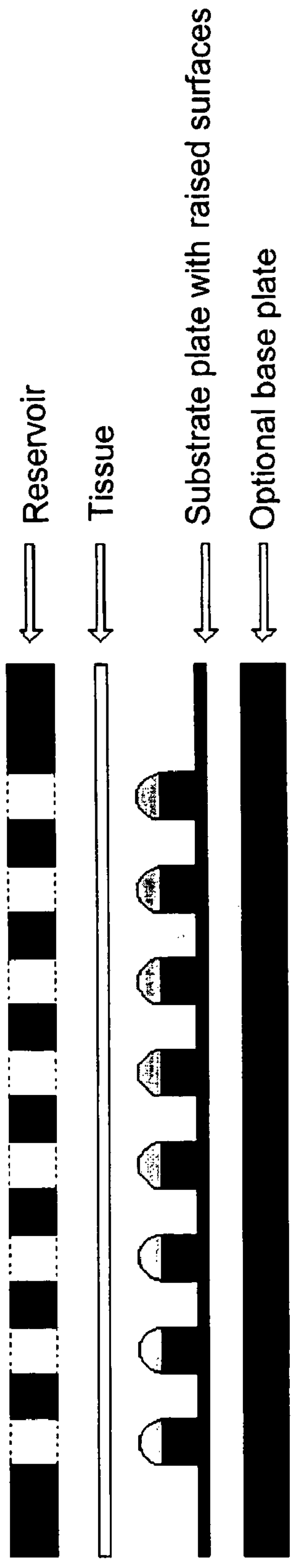
FIG. 8A is a cross-sectional view and FIG. 8B is an angled view, of a transdermal device comprising a reservoir plate on top of a tissue sample that overlays an array of samples on the raised pads of an assay plate supported by an optional base plate.
Figure 8B:
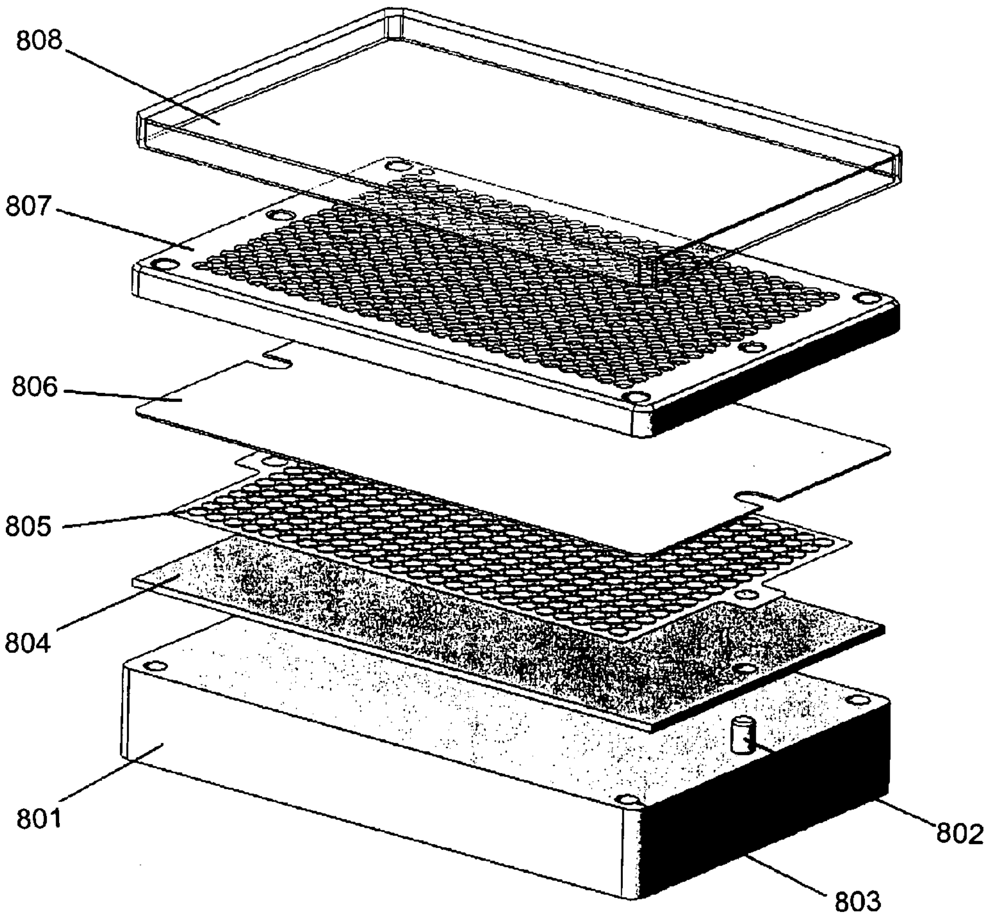

A first exemplified transdermal device is shown in FIG. 8A. A second exemplified transdermal device as shown in FIG. 8B shows a magnetic base plate 801 with guide pin 802 and threaded holes 803 for securing device. A magnet 804 is placed on top of base plate followed by substrate plate with an array of 384 raised pad sample receiving surfaces. A tissue sample 806 overlays the substrate plate with an array of samples (samples not shown) on the array of raised pad sample receiving surfaces. A 384 hole reservoir plate 807 is placed on top of the tissue sample. Once secured, reservoir fluid is added to reservoirs or wells created by placing the reservoir plate on top of the tissue sample. An optional lid 808 may be placed on top of the reservoir plate to prevent or impede evaporation of the reservoir fluid.

Transfer or flux of components from sample wells across tissue (i.e., tissue barrier transfer or diffusion) may be analyzed by measuring component concentration in specimens taken from reservoirs. Comparison of measurements taken from different samples/reservoirs aids in determining optimal sample compositions for improving tissue transfer or diffusion of a desired component (e.g., a pharmaceutical).

In use, the transdermal device of FIGS. 8A and 8B contains reservoir medium, above the sample tissue in the reservoirs if the reservoir plate and samples below tissue on raised pad sample receiving surfaces of the array.

As used herein, the term "active component" means a substance or compound that imparts a primary utility to a composition or formulation when the composition or formulation is used for its intended purpose. Examples of active components include pharmaceuticals, dietary supplements, alternative medicines, and nutraceuticals. Active components can optionally be sensory compounds, agrochemicals (including herbicides, pesticides, and fertilizers), the active component of a consumer product formulation, or the active component of an industrial product formulation. As used herein, an "inactive component" means a component that is useful or potentially useful to serve in a composition or formulation for administration of an active component, but does not significantly share in the active properties of the active component or give rise to the primary utility for the composition or formulation. Examples of suitable inactive components include, but are not limited to, enhancers, excipients, carriers, solvents, diluents, stabilizers, additives, adhesives, and combinations thereof.

According to the invention described herein, the "physical state" of a component is initially defined by whether the component is a liquid or a solid. If a component is a solid, the physical state is further defined by the particle size and whether the component is crystalline or amorphous. If the component is crystalline, the physical state is further divided into: (1) whether the crystal matrix includes a co-adduct or whether the crystal matrix originally included a co-adduct, but the co-adduct was removed leaving behind a vacancy; (2) crystal habit; (3) morphology, i.e., crystal habit and size distribution; and (4) internal structure (polymorphism). In a co-adduct, the crystal matrix can include either a stoichiometric or non-stoichiometric amount of the adduct, for example, a crystallization solvent or water, i.e., a solvate or a hydrate. Non-stoichiometric solvates and hydrates include inclusions or clathrates, that is, where a solvent or water is trapped at random intervals within the crystal matrix, for example, in channels. A stoichiometric solvate or hydrate is where a crystal matrix includes a solvent or water at specific sites in a specific ratio. That is, the solvent or water molecule is part of the crystal matrix in a defined arrangement. Additionally, the physical state of a crystal matrix can change by removing a co-adduct, originally present in the crystal matrix. For example, if a solvent or water is removed from a solvate or a hydrate, a hole will be formed within the crystal matrix, thereby forming a new physical state. The crystal habit is the description of the outer appearance of an individual crystal, for example, a crystal may have a cubic, tetragonal, orthorhombic, monoclinic, triclinic, rhomboidal, or hexagonal shape. The processing characteristics are affected by crystal habit. The internal structure of a crystal refers to the crystalline form or polymorphism. A given compound may exist as different polymorphs, that is, distinct crystalline species. In general, different polymorphs of a given compound are as different in structure and properties as the crystals of two different compounds. Solubility, melting point, density, hardness, crystal shape, optical and electrical properties, vapor pressure, and stability, etc. all vary with the polymorphic form.

As mentioned above, the component-in-common can be either an active component, such as a pharmaceutical, dietary supplement, alternative medicine, nutraceutical, agrochemical, other chemical or molecule of interest or an inactive component. In a preferred embodiment of the present invention, the component-in-common is an active component, and more preferably a pharmaceutical. As used herein, the term "pharmaceutical" means any substance or compound that has a therapeutic, disease preventive, diagnostic, or prophylactic effect when administered to an animal or a human. The term pharmaceutical includes prescription drugs and over the counter drugs. Pharmaceuticals suitable for use in the invention include all those known or to be developed.

Various types of penetration enhancers may be used to enhance transdermal transport of drugs. Penetration enhancers can be divided into chemical enhancers and mechanical enhancers, each of which is described in more detail below.

Chemical enhancers improve molecular transport rates across tissues or membranes by a variety of mechanisms. In the present invention, chemical enhancers are preferably used to decrease the barrier properties of the stratum corneum. Drug interactions include modifying the drug into a more permeable state (a prodrug), which would then be metabolized inside the body back to its original form (6-fluorouracil, hydrocortisone) (Hadgraft, 1985); or increasing drug solubilities (ethanol, propylene glycol). Despite a great deal of research (well over 200 compounds have been studied) (Chattaraj and Walker, 1995), there are still no universally applicable mechanistic theories for the chemical enhancement of molecular transport. Most of the published work in chemical enhancers has been done largely based on experience and on a trial-and-error basis (Johnson, 1996).

Many different classes of chemical enhancers used in the present invention have been identified, including cationic, anionic, and nonionic surfactants (sodium dodecyl sulfate, polyoxamers); fatty acids and alcohols (ethanol, oleic acid, lauric acid, liposomes); anticholinergic agents (benzilonium bromide, oxyphenonium bromide); alkanones (n-heptane); amides (urea, N,N-diethyl-m-toluamide); fatty acid esters (n-butyrate); organic acids (citric acid); polyols (ethylene glycol, glycerol); sulfoxides (dimethylsulfoxide); and terpenes (cyclohexene) (Hadgraft and Guy, 1989; Walters, 1989; Williams and Barry, 1992; Chattaraj and Walker, 1995). Most of these enhancers interact either with the skin or with the drug. Those enhancers interacting with the skin are herein termed "lipid permeation enhancers", and include interactions with the skin include enhancer partitioning into the stratum corneum, causing disruption of the lipid bilayers (azone, ethanol, lauric acid), binding and disruption of the proteins within the stratum corneum (sodium dodecyl sulfate, dimethyl sulfoxide), or hydration of the lipid bilayers (urea, benzilonium bromide). Other chemical enhancers work to increase the transdermal delivery of a drug by increasing the drug solubility in its vehicle (hereinafter termed "solubility enhancers"). Lipid permeation enhancers, solubility enhancers, and combinations of enhancers (also termed "binary systems") are discussed in more detail below.

Chemicals which enhance permeability through lipids are known and commercially available. For example, ethanol increases the solubility of some drugs up to 10,000-fold and yield a 140-fold flux increase of estradiol, while unsaturated fatty acids increase the fluidity of lipid bilayers (Bronaugh and Maibach, editors (Marcel Dekker 1989) pp. 1-12. Examples of fatty acids which disrupt lipid bilayer include linoleic acid, capric acid, lauric acid, and neodecanoic acid, which can be in a solvent such as ethanol or propylene glycol. Evaluation of published permeation data utilizing lipid bilayer disrupting agents agrees very well with the observation of a size dependence of permeation enhancement for lipophilic compounds. The permeation enhancement of three bilayer disrupting compounds, capric acid, lauric acid, and neodecanoic acid, in propylene glycol has been reported by Aungst, et al. *Pharm. Res.* 7,712-718 (1990). They examined the permeability of four lipophilic compounds, benzoic acid (122 Da), testosterone (288 Da), naloxone (328 Da), and indomethacin (359 Da) through human skin. The permeability enhancement of each enhancer for each drug was calculated according to $E_{c/pg}=P_{e/pg}/P_{pg}$, where $P_{e/pg}$ is the drug permeability from the enhancer/propylene glycol formulation and $P_{pg}$ is the permeability from propylene glycol alone.

The primary mechanism by which unsaturated fatty acids, such as linoleic acid, are thought to enhance skin permeability is by disordering the intercellular lipid domain. For example, detailed structural studies of unsaturated fatty acids, such as oleic acid, have been performed utilizing differential scanning calorimetry (Barry *J. Controlled Release* 6,85-97 (1987)) and infrared spectroscopy (Ongpipattanankul, et al., *Pharm. Res.* 8, 350-354 (1991); Mark, et al., *J. Control. Rd.* 12, pgs. 67-75 (1990)). Oleic acid was found to disorder the highly ordered SC lipid bilayers, and to possibly form a separate, oil-like phase in the intercellular domain. SC Lipid bilayers disordered by unsaturated fatty acids or other bilayer disrupters may be similar in nature to fluid phase lipid bilayers.

A separated oil phase should have properties similar to a bulk oil phase. Much is known about transport of fluid bilayers and bulk oil phases. Specifically, diffusion coefficients in fluid phase, for example, dimyristoylphosphatidylcholine (DMPC) bilayers Clegg and Vaz In "Progress in Protein-Lipid Interactions" Watts, ed. (Elsevier, N.Y. 1985) 173-229; Tocanne, et al., *FEB* 257, 10-16 (1989) and in bulk oil phase Perry, et al., "Perry's Chemical Engineering Handbook" (McGraw-Hill, N.Y. 1984) are greater than those in the SC, and more importantly, they exhibit size dependencies which are considerably weaker than that of SC transport Kasting, et al., In: "Prodrugs: Topical and Ocular Delivery" Sloan. ed. (Marcel Dekker, N.Y. 1992) 117-161; *Ports and Guy, Pharm. Res.* 9, 663-339 (1992); Willschut, et al. *Chemosphere* 30, 1275-1296 (1995). As a result, the diffusion coefficient of a given solute will be greater in a fluid bilayer, such as DMPC, or a bulk oil phase than in the SC. Due to the strong size dependence of SC transport, diffusion in SC lipids is considerably slower for larger compounds, while transport in fluid DMPC bilayers and bulk oil phases is only moderately lower for larger compounds. The difference between the diffusion coefficient in the SC and those in fluid DMPC bilayers or bulk oil phases will be greater for larger solutes, and less for smaller compounds. Therefore, the enhancement ability of a bilayer disordering compound which can transform the SC lipids bilayers into a fluid bilayer phase or add a separate bulk oil phase should exhibit a size dependence, with smaller permeability enhancements for small compounds and larger enhancement for larger compounds.

Another way to increase the transdermal delivery of a drug is to use chemical solubility enhancers that increase the drug solubility in its vehicle. This can be achieved either through changing drug-vehicle interaction by introducing different excipients, or through changing drug crystallinity (Flynn and Weiner, 1993).

Solubility enhancers include water diols, such as propylene glycol and glycerol; mono-alcohols, such as ethanol, propanol, and higher alcohols; DMSO; d imethylformamide; N, N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones.

Some devices for delivery of an active component or drug across a tissue barrier, and in particular transdermal delivery devices such as transdermal patches, typically include an adhesive. The adhesive often forms the matrix in which the active component or drug is dissolved or dispersed and, of course, is meant to keep the device in intimate contact with the tissue, such as skin. Compatibility of the active component or drug with an adhesive is influenced by its solubility in that adhesive. Any supersaturated conditions produced in storage or in use are generally very stable against precipitation of the active component or drug within the adhesive matrix. A high solubility is desired in the adhesive to increase the driving force for permeation through the tissue and to improve the stability of the device.

Several classes of adhesive are used, each of which contain many possible forms of adhesives. These classes include polyisobutylene, silicone, and acrylic adhesives. Acrylic adhesives are available in many derivatized forms. Thus, it is often a very difficult problem to select which adhesive might be best to use with any particular drug and enhancer. Typically, all ingredients used in transdermal deliveryare dissolved in a solvent and cast or coated onto a plastic backing material. Evaporation of the solvent leaves a drug-containing adhesive film. The present invention enables rapid and efficient testing of the effects of various types and amounts of adhesives in a sample composition or formulation.

Solvents for the active component, carrier, or adhesive are selected based on biocompatibility as well as the solubility of the material to be dissolved, and where appropriate, interaction with the active component or agent to be delivered. For example, the ease with which the active component or agent is dissolved in the solvent and the lack of detrimental effects of the solvent on the active component or agent to be delivered are factors to consider in selecting the solvent. Aqueous solvents can be used to make matrices formed of water soluble polymers. Organic solvents will typically be used to dissolve hydrophobic and some hydrophilic polymers. Preferred organic solvents are volatile or have a relatively low boiling point or can be removed under vacuum and which are acceptable for administration to humans in trace amounts, such as methylene chloride. Other solvents, such as ethyl acetate, ethanol, methanol, dimethyl formamide (DMF), acetone, acetonitrile, tetrahydrofuran (THF), acetic acid, dimethyl sulfoxide (DMSO) and chloroform, and combinations thereof, also may be utilized. Preferred solvents are those rated as class 3 residual solvents by the Food and Drug Administration, as published in the Federal Register vol. 62, number 85, pp. 24301-24309 (May 1997). Solvents for drugs will typically be distilled water, buffered saline, Lactated Ringer's or some other pharmaceutically acceptable carrier.

The screening methods of the present invention identify, for example, 1) optimal compositions or formulations comprising one or more active components and one or more inactive components for achieving desired characteristics for such compositions or formulations, 2) optimal adhesive/enhancer/excipient compositions for compatibility with an active component or drug, 2) optimal active component or drug/adhesive/enhancer/additive compositions for maximum drug flux through stratum corneum, and 3) optimal active component or drug/adhesive/enhancer/additive compositions to minimize cytotoxicity.

As mentioned supra, a preferred method of using the tissue barrier transfer device of the present invention entails determining, directly or indirectly, the presence, absence or concentration of components (e.g. pharmaceuticals) that diffuse through tissue from samples on raised pads into reservoirs of the reservoir plate. Such measurements may be performed by a variety of means known to those skilled in the art. For example, any knowledge of spectroscopic technique can be used to determine presence, absence or concentration of a component-in-common. Suitable measurement techniques include, but are not limited to include HPLC, spectroscopy, infrared spectroscopy, near infrared spectroscopy, Raman spectroscopy, NMR, X-ray diffraction, neutron diffraction, powder X-ray diffraction, radiolabeling, and radioactivity. In one exemplary embodiment, and not by way of limitation, the passive permeabilities of active components (e.g. a drug) through human skin can be measured using trace quantities of radiolabelled active component or drug.

The permeability values can be calculated under steady-state conditions from the relationship $P=(dN_r/dt)/(AC_d)$ where A is the surface area of the tissue accessible to a sample, $C_d$ is the component or drug concentration in the sample, and $N_r$ is the cumulative amount of component or drug which has permeated into the receptor reservoir.

According to a preferred embodiment of the invention, diffusion data related to inhomogeneous tissue segments or tissue defects, may be discarded to avoid inaccurate measurements. Alternatively, if the effect of defects in a tissue segment can be characterized and/or quantified, associated diffusion measurements can be mathematically adjusted to account for the defects. In another embodiment of the invention, defects in a tissue specimen are repaired by feeding the defect locations to an ink jet printer that is instructed to print wax to cover these locations.

The foregoing descriptions of specific embodiments of the present invention are presented for purposes of illustration and description. They are not intended to be exhaustive or to limit the invention to the precise forms disclosed. Obviously many modifications and variations are possible in view of the above teachings. For example, the substrate may be flexible to allow the array of samples to be conformed around an experimental set-up, specifically to be used in-vivo on an animal tissue during array-based transdermal sensitization testing. Also, the topology and roughness of the sample receiving surface should be less than 5 μm. The embodiments were chosen and described in order to best explain the principles of the invention and its practical applications, to thereby enable others skilled in the art to best utilize the invention and various embodiments with various modifications as are suited to the particular use contemplated. Furthermore, the order of steps in the method are not necessarily intended to occur in the sequence laid out. Just as each embodiment disclosed herein may be included as an embodiment of the present invention, each embodiment set forth herein may be specifically excluded from the present invention as claimed. It is intended that the scope of the invention be defined by the following claims and their equivalents. In addition, any references cited above are incorporated herein by reference.

What is claimed is:

1. A method of using an assay plate on an animal, comprising:

providing a flexible substrate having a flexible substrate surface and a rigid raised pad extending laterally from said flexible substrate surface, wherein said raised pad has a substantially planar sample receiving surface configured for receiving a sample thereon, a sharp edge at a junction between a sidewall coupling said sample receiving surface to said substrate surface, and no wall extending beyond and surrounding said sample receiving surface;

depositing a sample on said sample receiving surface;

attaching said flexible substrate onto an animal in order for said sample to contact skin of said animal; and performing an experiment on said animal in response to an effect caused by said sample.

2. The method of claim 1, further comprising drying said sample before said performing an experiment.

3. The method of claim 2, further comprising, after said drying, depositing a different sample on said raised pad and drying said different sample.

4. The method of claim 2, further comprising, after said drying, redepositing said sample on said raised pad and redrying said sample.

5. The method of claim 1, wherein said depositing comprises depositing an amount of sample on said pad sufficient to form a raised droplet without substantially spilling off said sample receiving surface.

6. The method of claim 1, further comprising etching a material to form said substrate and said raised pad.

7. The method of claim 1, further comprising injection molding or casting said raised pad and said substrate.

8. The method of claim 1, further comprising overlaying said sample with a membrane or tissue that is not said skin of said animal.

9. A method of determining optimal medical device compositions or formulations, comprising:

preparing an array of samples supported by a planar sample receiving surface of an assay plate comprising a first lower member comprising a substrate having a substrate surface; a plurality of raised pads extending from said substrate surface, each raised pad having a substantially planar sample receiving surface configured for holding a sample thereon for in situ experimentation; and a second upper member comprising a reservoir plate having an array of openings, that when secured, are aligned with said planar sample receiving surface forming to form wells or reservoirs, each sample comprising an active component and at least one additional component, wherein each sample differs from at least one other sample with respect to at least one of:

(i) the identity of the active component, (ii) the identity of the additional components, (iii) the ratio of the active component to the additional component, or (iv) the physical state of the active component;

securing a reservoir plate to the planar sample receiving surface, the reservoir plate having an array of holes that when secured are aligned with said planar sample receiving surface forming wells or reservoirs;

filling the array of reservoirs with a reservoir medium; and determining rate of release of the active component from each sample in said array of samples into the reservoir medium to determine an optimal medical device formulation.

10. The method of claim 9, wherein said reservoir plate is secured on top of said assay plate.

11. The method of claim 9, wherein the size or diameter of the holes or openings of the reservoir plate are smaller than the size or diameter of the raised pads.

* * * * *